(12) United States Patent  (10) Patent No.: US 7,997,049 B2
Moodley  (45) Date of Patent: Aug. 16, 2011

(54) PROCESS AND MACHINE FOR AUTOMATED MANUFACTURE OF GASTRO-RETENTIVE CAPSULES

(75) Inventor: Jagathesan Moodley, Co. Athlone (IE)

(73) Assignee: Merrion Research III Limited (IE)

( * ) Notice: Subject to any disclaimer, the term of this patent is extended or adjusted under 35 U.S.C. 154(b) by 0 days.

(21) Appl. No.: 12/397,492

(22) Filed: Mar. 4, 2009

(65) Prior Publication Data

US 2009/0158696 A1  Jun. 25, 2009

Related U.S. Application Data

(62) Division of application No. 10/566,458, filed on Jan. 30, 2006, now Pat. No. 7,513,091.

(60) Provisional application No. 60/491,157, filed on Jul. 30, 2003.

(51) Int. Cl.
B65B 63/04  (2006.01)
B65B 7/28  (2006.01)

(52) U.S. Cl. ........... 53/429; 53/471; 53/449; 53/454; 53/116; 53/281

(58) Field of Classification Search .......... 53/428, 53/429, 471, 454, 438, 116, 122, 529; 424/468, 424/473, 43, 457
See application file for complete search history.

(56) References Cited

U.S. PATENT DOCUMENTS

| | | | |
|---|---|---|---|
| 3,786,813 A | 1/1974 | Michaels | |
| 3,944,064 A | 3/1976 | Bashaw et al. | |
| 4,055,178 A | 10/1977 | Harrigan | |
| 4,207,890 A | 6/1980 | Mamajek et al. | |
| 4,285,987 A | 8/1981 | Ayer et al. | |
| 4,595,583 A | 6/1986 | Eckenhoff et al. | |
| 4,773,907 A | 9/1988 | Urquhart et al. | |
| 4,996,058 A | 2/1991 | Sinnreich | |
| 5,198,229 A | 3/1993 | Wong et al. | |
| 5,417,030 A | 5/1995 | Ribani et al. | |
| 5,817,335 A | 10/1998 | Wong et al. | |
| 5,966,910 A | 10/1999 | Ribiani et al. | 53/560 |
| 6,120,801 A | 9/2000 | Parekh et al. | 424/463 |
| 6,120,803 A | 9/2000 | Wong et al. | |
| 6,245,350 B1 | 6/2001 | Amey et al. | 424/456 |
| 6,656,501 B1 | 12/2003 | Cooker | |
| 6,669,954 B2 * | 12/2003 | Crison et al. | 424/456 |
| 7,066,945 B2 * | 6/2006 | Hashiba et al. | 606/191 |
| 7,445,795 B2 * | 11/2008 | Bakhshaee et al. | 424/451 |
| 7,524,515 B2 * | 4/2009 | Roberts | 424/490 |
| 7,670,612 B2 * | 3/2010 | Miller | 424/400 |

\* cited by examiner

*Primary Examiner* — Paul R Durand

(74) *Attorney, Agent, or Firm* — Myers Bigel Sibley & Sajovec, PA

(57) ABSTRACT

A process and apparatus for making a gastro-retentive device (10). The method includes the steps of providing a pouch assembly having an ingredient section within a membrane; folding the membrane to form a folded pouch assembly; inserting the folded pouch assembly into a first capsule section (20a) to form a pouch/first capsule assembly, and inserting the pouch/first capsule assembly into a second capsule section (20b). Also provided is an apparatus (38) for carrying out the above method which includes a tooling block (44) having a passageway (62) configured for slidable movement of the pouch assembly (18) therein, and a tooling pocket (60) extending from a top surface of the tooling block to the passageway and which receives the pouch assembly. A ram (86) is provided for pushing the pouch assembly through the tooling pocket into the passageway, wherein the pouch assembly is folded and encapsulated.

8 Claims, 24 Drawing Sheets

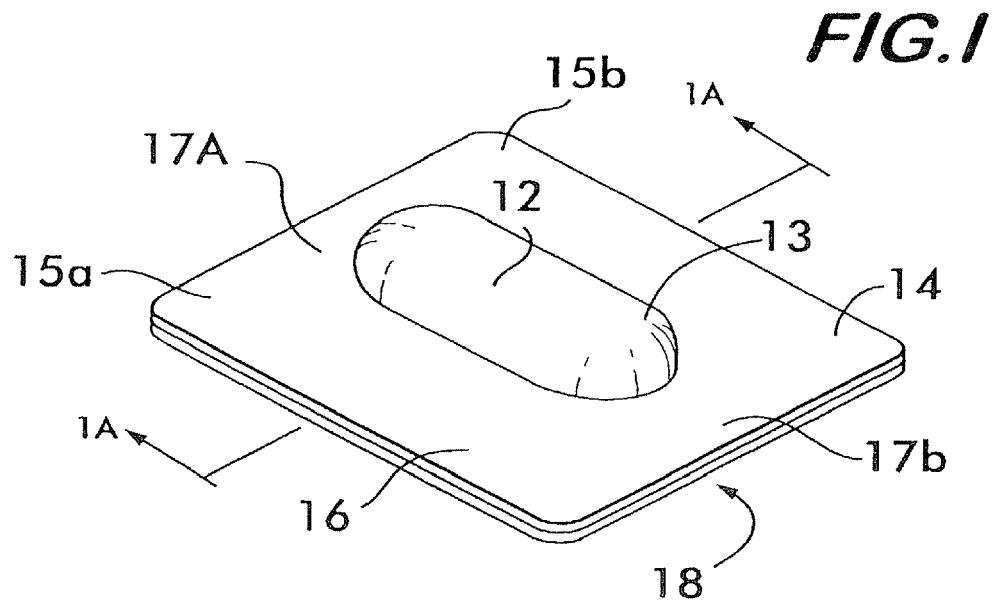
FIG.1
FIG.1A
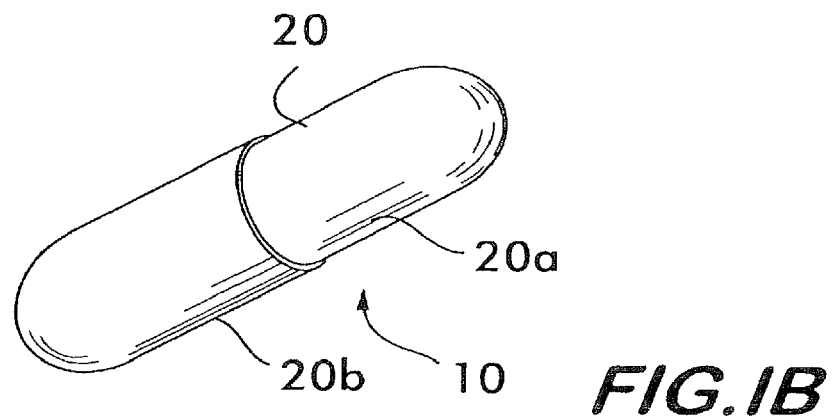
FIG.1B

PROCESS AND MACHINE FOR AUTOMATED MANUFACTURE OF GASTRO-RETENTIVE CAPSULES

CROSS-REFERENCE TO RELATED APPLICATIONS

This application is a divisional application of U.S. patent application Ser. No. 10/566,458, filed on Jan. 30, 2006 now U.S. Pat. No. 7,513,091 which claims the priority of U.S. Provisional Application No. 60/491,157 filed Jul. 30, 2003, which is hereby incorporated herein by reference.

BACKGROUND

The present invention relates to a process and an apparatus for the automated manufacture of a gastro-retentive device. An example of such a device is a retard form of the type disclosed in U.S. Pat. No. 4,996,058, which is hereby incorporated herein by reference, although the present invention is not limited to such retard forms, but is applicable to any gastro-retentive device.

The term "retard form," denotes a dosage form which effects delayed release of at least a portion of the active ingredient in the stomach and to the upper part of the small intestine in comparison to conventional dosage forms, such as customary tablets or capsules. Avoiding an undesirably high initial dose, the release is effected continuously over a relatively long period and controlled at an effective level. The retard form is administered orally and, once in contact with the stomach fluids, expands so as to float on the stomach fluids and/or be retained within the space of the stomach due to its size following inflation, which precludes passage across the pylorus sphincter. In this manner it remains in the stomach to insure continuous controlled release of the physiologically active ingredients.

A retard form is characterized preferably, at least in one form, by the following: (a) at least one component that expands on contact with bodily fluid (e.g., a substance that generates or constitutes a blowing agent), and/or a physiologically active substance, and/or a combination of physiologically active substances, and/or optionally a pharmaceutically acceptable hydrophilic swelling agent and further pharmaceutically acceptable adjuncts, (b) at least one hydrophilic membrane which surrounds component (a) and which is expansible at the site of use and is permeable to body fluid, and (c) a covering which surrounds component (a) and membrane (b) and which disintegrates without delay under the action of bodily fluid at the site of use in the stomach, e.g., a gelatin capsule.

As an example, a retard form of this type suitable for the present invention could take the following form. A component (a) is provided in the form of a tablet surrounded by and sealed within component (b) in the form of a hydrophilic membrane or film, the membrane forming a pouch in which the tablet sits. The tablet and membrane assembly are fitted within component (c) provided in the form of a gelatin capsule.

Taken orally, the retard form moves to the stomach where the gelatin capsule disintegrates to release the tablet membrane assembly. Upon contact with stomach fluid, the tablet generates the blowing agent, for example carbon dioxide gas. The gas causes the membrane surrounding the tablet to inflate, forming a gas-filled "bag." This gas-filled "bag" is able to float on the stomach fluids and/or is unable to pass through the pylorus sphincter following inflation, and thus is retained in the stomach. During its dwell time in the stomach, any active ingredients present in the tablet are released slowly and/or in a controlled manner into the surrounding body fluid, preferably by diffusion, through the membrane. Since gastric juice is being transported further into the upper part of the small intestine, the active ingredient passes continuously and over a prolonged period into the duodenum and jejunum, where it can be absorbed over an extended period. The retard form ensures continuous release of any active ingredient in conjunction with uniform absorption, or at least that the device will remain in the stomach for the desired time period. Once the gas generating components are used up, and/or the when the "bag" deflates to a certain size, this allows the remainder of the device to pass through the body.

The manufacture of a gastro-retentive device of the general type described above can be complex and includes several challenges. The component(s) (a) or tablet must be sealed within the membrane(s) to form the pouch. Depending on the drug or drugs of choice, the tablet may also contain other excipients which control the release of the drug or drugs from the tablet into the medium of the pouch and subsequently into the gastric fluid of the stomach following diffusion across the pouch. Once formed, the pouch must be folded to fit within the capsule. While such gastro-retentive devices can be produced manually, it is believed that an automated and economical process for producing such forms will help bring the benefits of gastro-retentive devices to the public.

SUMMARY OF THE INVENTION

The present invention provides methods and apparatuses for the automated manufacture of gastro-retentive devices that require folding or wrapping for insertion into a capsule. The gastro-retentive devices to be wrapped and encapsulated preferably have at least the following components: 1) an ingredient section, 2) a membrane surrounding the ingredient section so as to form a pouch that has at least one flap extending from the ingredient section (the ingredient section in combination with the membrane is referred to as a "pouch assembly"), and a capsule surrounding the pouch assembly and which is capable of disintegrating upon contact with bodily fluids to release the pouch assembly, the capsule having first and second capsule sections.

In one embodiment, the process includes the following steps: providing a strip of the pouch assemblies; separating a pouch assembly from the strip; placing the pouch assembly on a tooling block having i) a surface and ii) a pocket formed therein which is sized for receiving the pouch assembly; positioning the pouch assembly such that the ingredient section is placed over the pocket with the flap extending away from the pocket; folding at least one of the flaps by pushing the ingredient section of the pouch assembly into the pocket; inserting the folded pouch assembly into the first cap section to form a pouch/first cap assembly; and connecting the pouch/first cap assembly to the second cap section to fully encapsulate the pouch.

An apparatus for the manufacture of a gastro-retentive device is also provided. In one embodiment, the apparatus includes a tooling block having a passageway extending therethrough, and a tooling pocket extending from a surface of the tooling block to the passageway and which is configured for receiving the pouch assembly. A push rod, such as a ram, is disposed to push the pouch assembly through the tooling pocket into the passageway. At least one folding member, such as an arm, is provided for folding the flap of the pouch assembly extending from the passageway of the tooling block, the folding arm being moveable relative to the tooling block. A push rod is disposed for pushing the pouch assembly through the passageway into the first cap section, and another push rod is disposed on the apparatus for pushing the pouch assembly through the passageway into the second cap section.

BRIEF DESCRIPTION OF THE DRAWINGS

The following detailed description will be better understood when read in conjunction with the figures appended hereto. For the purpose of illustrating the invention, there is shown in the drawings a preferred embodiment. It is understood, however, that this invention is not limited to this embodiment or the precise arrangements shown.

FIG. 1 is a perspective view of an ingredient/pouch assembly for an exemplary gastro-retentive device;

FIG. 1A is a cross sectional view taken along line 1A-1A in FIG. 1;

FIG. 1B is a perspective view of the encapsulated gastro-retentive device with the ingredient/pouch assembly of FIG. 1 inside the capsule;

DETAILED DESCRIPTION OF THE INVENTION

Figure 2:
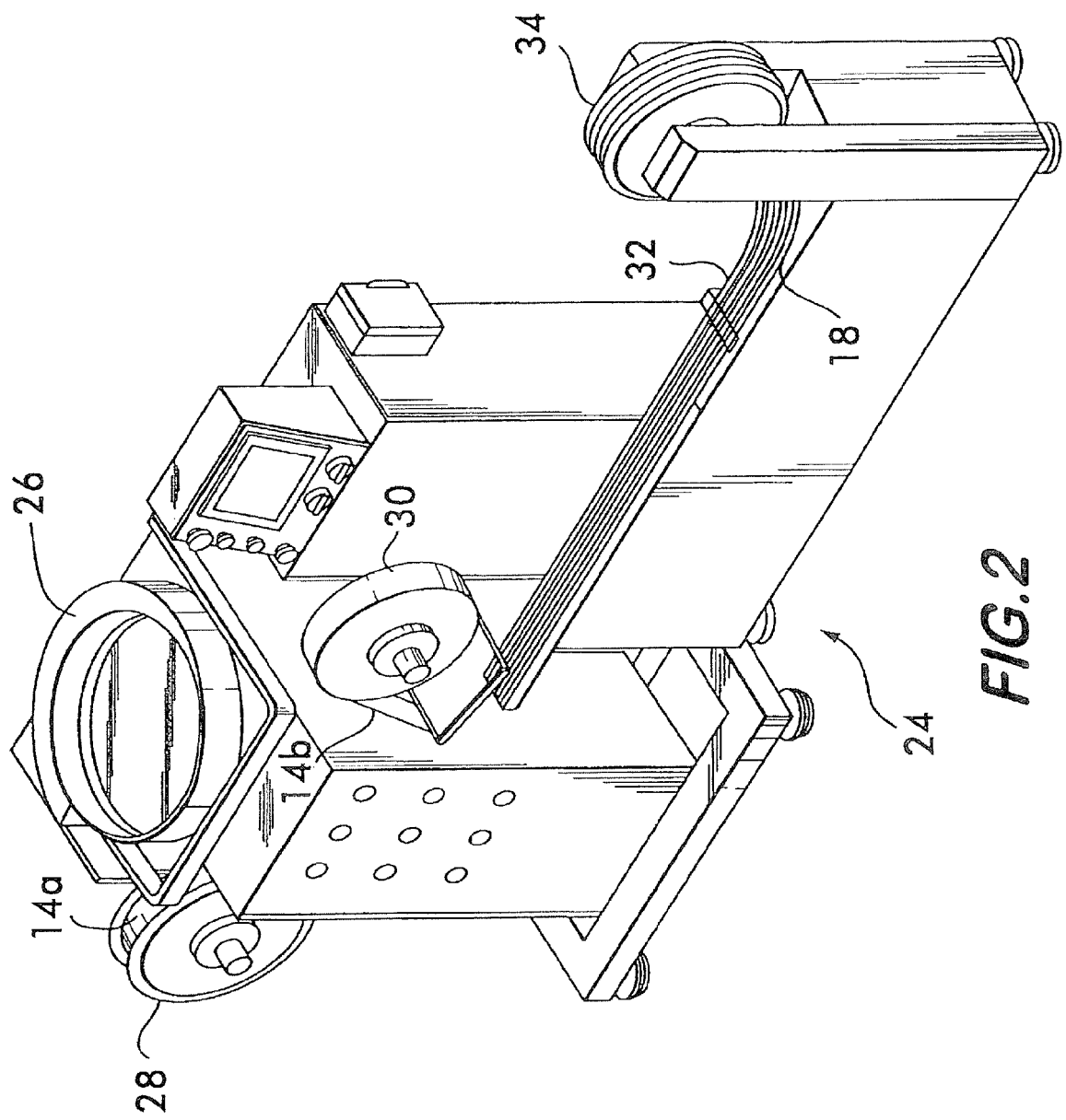
FIG. 2 is a perspective view of an ingredient/pouch packaging machine.

The present invention provides novel methods and apparatuses for making gastro-retentive devices. The methods and apparatuses of the present invention permit automation of the manufacturing process and thus allow the economical manufacture of such devices.

An exemplary gastro-retentive device 10 to be manufactured in accordance with the present invention is illustrated with reference to FIGS. 1, 1A and 1B. FIG. 1B shows the completed encapsulated gastro-retentive device 10 which is now described in further detail.

With particular reference to FIGS. 1 and 1A, the gastro-retentive device contains the desired active ingredients. The term active ingredient is used herein in its broadest sense to include any component or combination of components which have a functional character with respect to operation of the device. For example, active ingredients can include any one or more of physiologically active ingredients, excipients, blowing agents, or similar possibilities as discussed above in the background section as component (a). The active ingredient is preferably provided in a centralized or common ingredient section 12 of the device 10, and which is preferably provided in the form of a tablet 13. The tablet 13 is preferably formed in a flattened capsule shape such as a deep or normal concave caplet shape. While it is contemplated that all dimensions for the tablet 13 are available for use in accordance with the present invention in certain preferred embodiments, the active ingredient is preferably in a form having dimensions of about 3 mm height and length and width of about 16 mm long by 6 mm wide. Nominal tablet weight is 640-750 mg, and tablet hardness approximately 50 Newtons. Other shapes, sizes, weights, hardness and configurations are suitable depending on the desired use. While a solid tablet 13 is used for illustration purposes herein, it is understood that other forms of the ingredient section 12 may be used and that the present invention is not limited in its broad aspect to tablets.

Surrounding the ingredient section 12 is a film or membrane 14 (an example being component (b) as described in the background section), configured to form a pouch 16 which is inflatable upon the activation of an expansion agent, such as a component which functions to cause the generation of gas from the ingredient section 12 within, to form an expanded or gas-filled "bag." The membrane is preferably provided in two layers, a bottom layer 14a and top layer 14b, with the ingredient section 12 sandwiched in between. The two membrane layers 14a, 14b are preferably heat sealed to form a sealed pouch 16. The areas of the pouch surrounding the ingredient section 12 are referred to as flaps, e.g., flaps 15a and 15b as shown. (There may also be front and back flaps 17a, 17b). The flaps preferably include any evacuated portion of the pouch extending outside the ingredient section 12. The membrane film preferred is a polyvinylaclcohol (PVA), preferably has a thickness of approximately 150 μm (±10 μm), and may be formed of two membrane layers sealed together. The pouch 16 is preferably between about 20 mm×20 mm and 25 mm×25 mm inside dimensions, although other sizes are suitable depending on the desired use. The seal width is preferably about 2 mm to 3 mm in addition to the inside dimensions indicated all around the pouch. The combination of the ingredient section 12 and pouch 16 will be referred to herein as the ingredient/pouch assembly 18, or pouch assembly, as shown in FIGS. 1 and 1A. The corners of the pouch assembly 18 are preferably rounded as shown to help prevent damage during processing.

Surrounding the ingredient/pouch assembly 18 is a capsule or capsule like container 20 (component (c) as discussed in the background section) having a first capsule section 20a (the capsule body), and a second capsule section 20b (the capsule cap). See FIG. 1B. The capsule 20 disintegrates quickly when exposed to the stomach fluids to release the pouch assembly 18. The capsule is preferably gelatin, having a size range suitable to contain the ingredient section 12 and pouch, sizes 0EL and 00EL being preferred for the illustrated embodiment. The pouch assembly 18 is fitted inside the capsule in a folded, compact form. Once the capsule disintegrates, the pouch assembly 18 contacts the bodily fluids and expands or inflates to form the "bag" as described previously.

One preferred method of making the gastro-retentive device 10 of the present invention (described below) begins with the manufacture of the pouch assembly 18. Shown in FIG. 2 is a pouch packaging machine 24 for producing a strip of attached ingredient/pouch assemblies 32, each of the assemblies preferably being of the type illustrated in FIGS. 1 and 1A and which use a tablet 13 for the ingredient section 12. A tablet hopper 26 or similar device receives and holds the tablets 13 which are produced through methods known in the art. A first spool 28 of film is provided for forming the first or lower membrane layer 14a, and a second spool 30 of film is provided for forming the second or upper membrane layer 14b. The spools are preferably automatically maintained at the proper tension.

A tablet 13 is controllably released from the hopper 26 onto the lower membrane layer 14a in the desired orientation. The upper membrane layer 14b is then laid on top of the tablet 13. (With films that have a backing, the backing is preferably rewound for removal and disposal). The machine 24 automatically punches a hole in at least one of the films 14a, 14b through which air can be evacuated during a subsequent sealing process. Alternatives are possible. With the tablet sandwiched between the two films 14a, 14b, the films are pressed together and the air between the two layers evacuated through the punched hole to a desired vacuum level.

The two films are then sealed together, preferably with a heating element pressed into contact with the film to produce a heat seal around the tablet 13, preferably air tight, of about 2 to 3 mm in width (the air evacuation hole being on the outside of the seal), thereby forming the sealed tablet/pouch assembly 18. The sealing temperature is preferably between about 200° C. to about 210° C. with a dwell time of about two seconds. The machine 24 can produce multiple tablet/pouch assemblies 18 during each cycle, the completed tablet/pouch assemblies forming a continuous strip 32 of tablet/pouch assemblies 18 which can be rolled up into a spool 34, or fed directly to a tablet pouch fold encapsulation machine for further processing as described below. The machine 24 can be controlled by a programmable controller as is known in the art. Other known evacuation and sealing methods are contemplated. For example, three of the four sides of the films/tablet assembly could be heat sealed first, then the air evacuated from the pressed films/tablet assembly on the unsealed side, followed by sealing the last side. Moreover, the tablet can be inserted into the pouch after the three sides are sealed, the fourth side then being sealed after the tablet is inserted and the air evacuated by vacuum.

Other means of making the tablet/pouch assembly 18 are known. For example, a customized machine from Prodo-Pak Corporation of Garfield, N.J., model number RV 925 WS-4 pouch forming and sealing machine, can be used.

Figure 3:
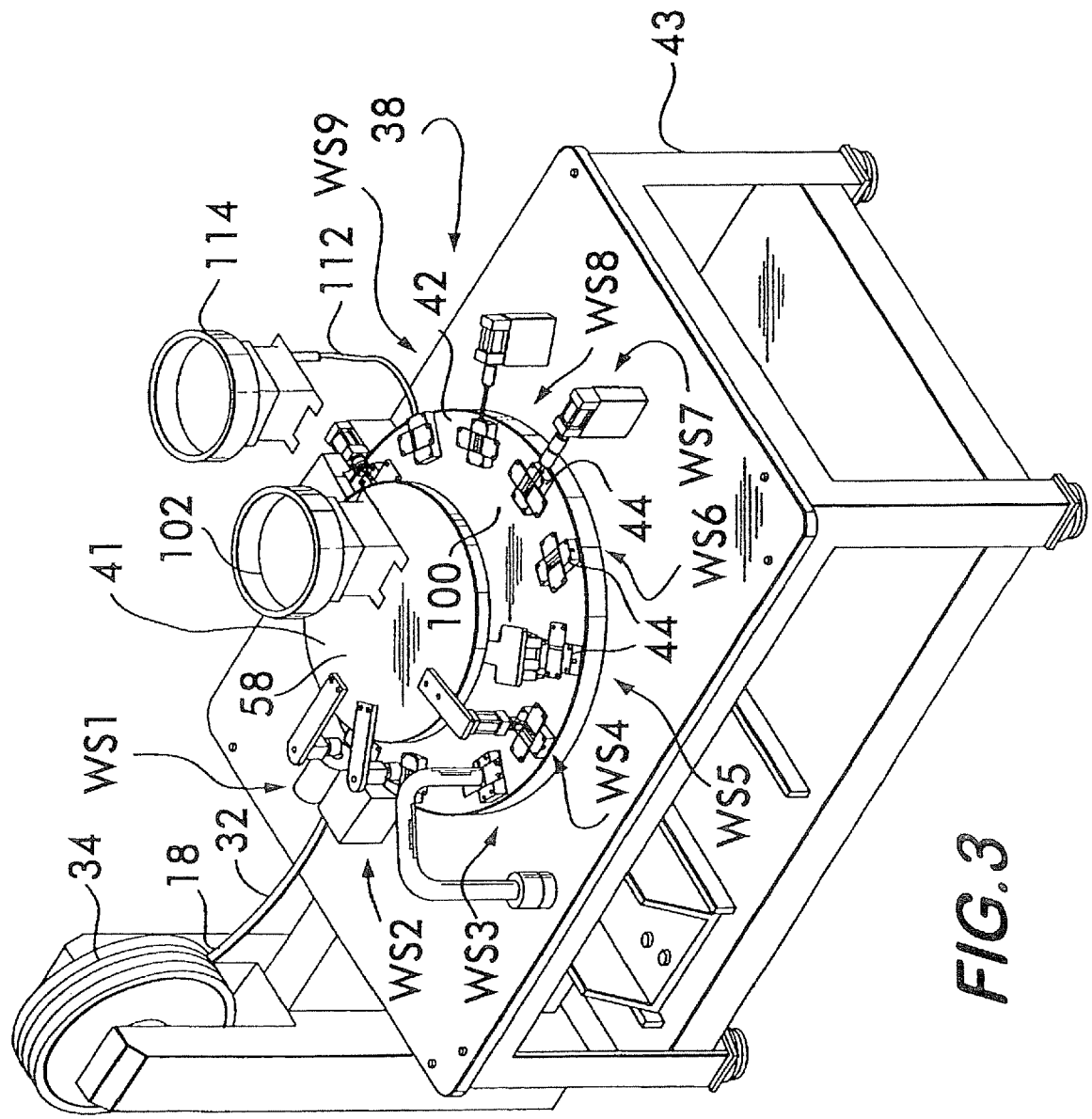
FIG. 3 is a perspective view of an encapsulation machine of the present invention.

With reference to FIG. 3, a pouch assembly fold and encapsulation machine 38 is now described. The encapsulation machine 38 receives the pouch assembly 18 and, through the steps described below, which are preferably carried out in an automated and/or computer controlled fashion, produces an encapsulated pouch assembly (retard dosage form 10). As seen in FIG. 3, the machine 38 has a movable surface 41 which advances multiple tooling blocks 44 to multiple workstations (WS1 to WS11) located at different locations along the path of the movable surface for carrying out the manufacturing steps. In the illustrated embodiment, the movable surface 41 takes the form of a rotatable table 42 mounted on a frame 43. The tooling blocks 44 (see FIG. 4A) are preferably mounted along the outer edge of the table 42 as shown, each tooling block 44 capable of receiving and carrying at least one ingredient/pouch assembly 18 for processing. The table 42 rotates an index position to advance the ingredient/pouch assembly 18 to the different work stations preferably along a circular path where the various manufacturing steps are performed. An upper support table 58, which is preferably stationary, supports equipment as described below. The rotation of the table 42 is preferably controlled by a controller or other suitable automated means controlling a motor as is known in the art to move the ingredient/pouch assemblies 18 to the multiple work stations where the various steps are performed to produce the final encapsulated product 10.

Figure 4:
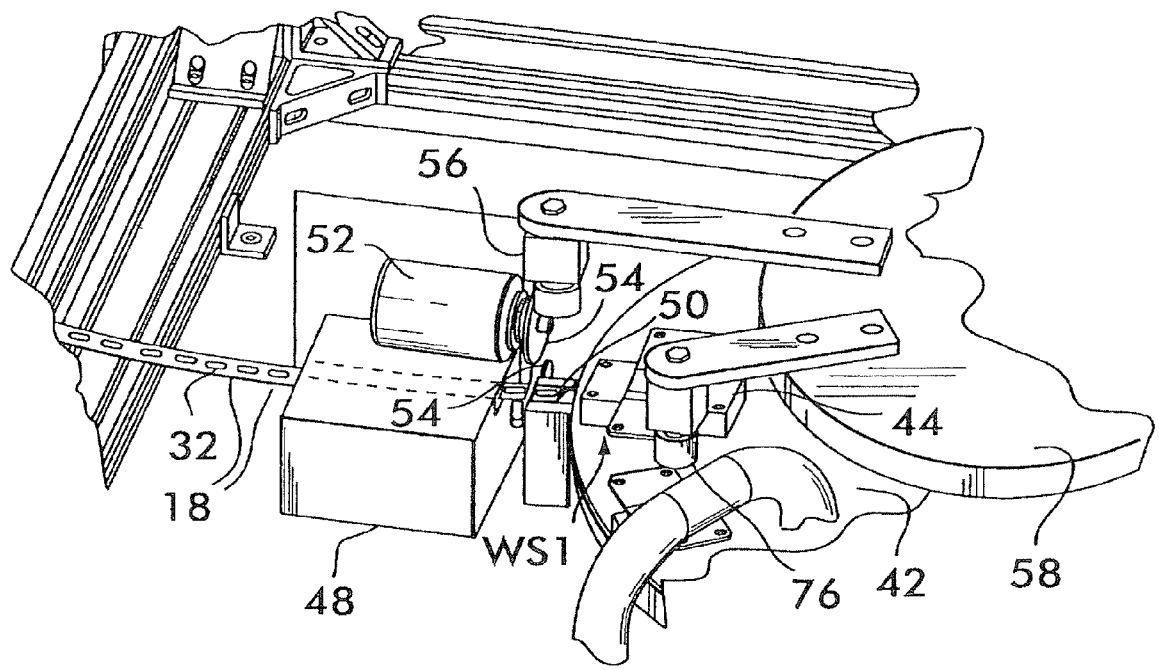
FIG. 4 is an illustration of work station 1 of the encapsulation machine shown in FIG. 3.

With reference to FIGS. 3 and 4, a strip 32 of pouch assemblies 18 is delivered to the machine 38 at a work station one (WS1) either directly from a pouch packaging machine, such as machine 24, from the spool 34 as shown in FIG. 3, or other suitable means. The strip 32 moves through a slotted strip puller or indexer 48 where a one or more pouch assemblies 18, resting on a slotted support shelf 50, is removed from the incoming strip 32 by cutter 52, such as the rotary cutter shown having blades 54 which shear the pouch or pouches from the strip. Any other suitable cutter may be used, such as pneumatically operated scissor like devices, or a laser. Any suitable means for providing pouch assemblies to the shelf 50 may be used, including means that do not require strips of pouches, but which place individual pouches onto the shelf 50.

Figure 4A:
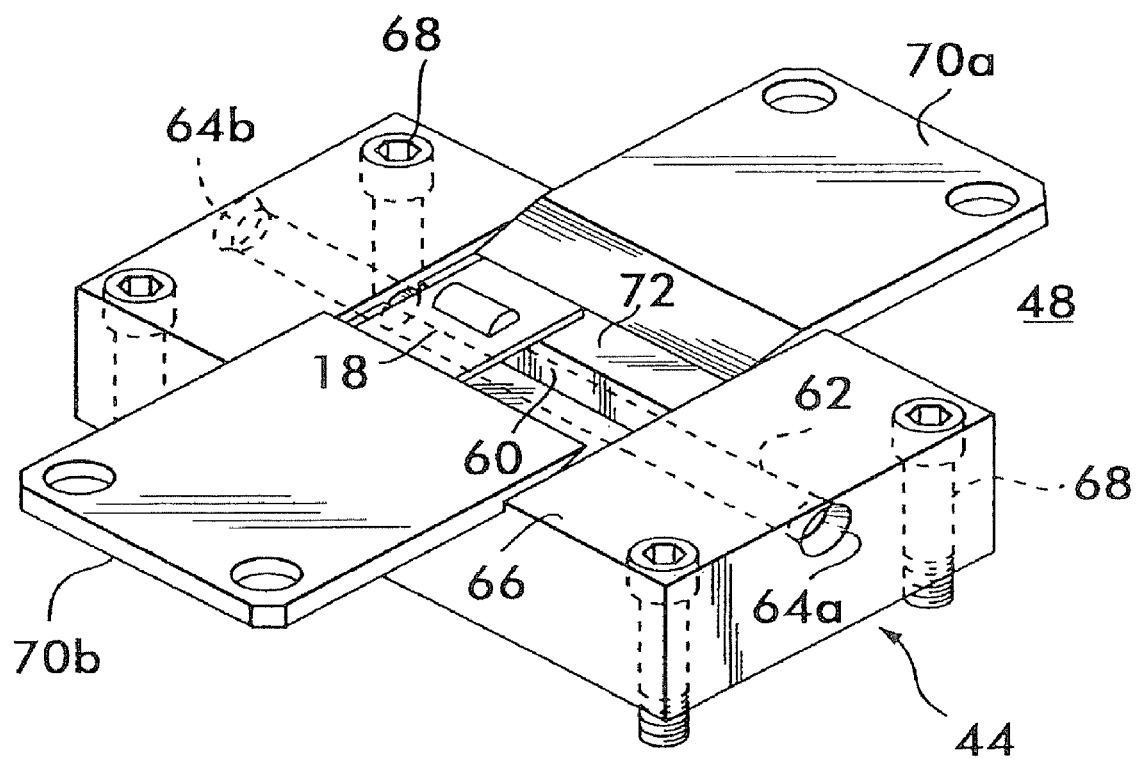
FIG. 4A is a detailed view of work station 1 showing the ingredient/pouch assembly on a tooling block.

With further reference to FIGS. 4 and 4A, a pick and place unit 56, such as that which uses a suction to pick and hold an item, and a vision system to control the placement, picks the removed pouch assembly 18 from the shelf 50 and places it on the tooling block 44 directly above an upper left portion of a tooling pocket 60 as seen in FIG. 4A. As seen in FIG. 4A, the tooling block 44 has a passageway 62, which is preferably cylindrical and extends longitudinally through the block 44, and which has openings 64a, 64b on both sides of the block 44. The tooling pocket 60 extends downward from an outer surface, preferably the top face 66 of the block 44, to the passageway 62 as shown. Bolts 68 connect the tooling block 44 to the table 42. Slidable on the top face 66 of the block 44 is at least one folding member adapted to engage at least one of the flaps of the pouch assembly and fold it. In the illustrated embodiment this folding member takes the form of left and right folding arms 70a, 70b, respectively. The folding arms 70a, 70b are slidable in the slightly recessed or grooved area 72 toward and away from the tooling pocket 60 for folding the ingredient/pouch assembly 18 as described below. The surface of the recessed area 72 is preferably at about the same elevation as the top of the passageway 62.

Figure 5:
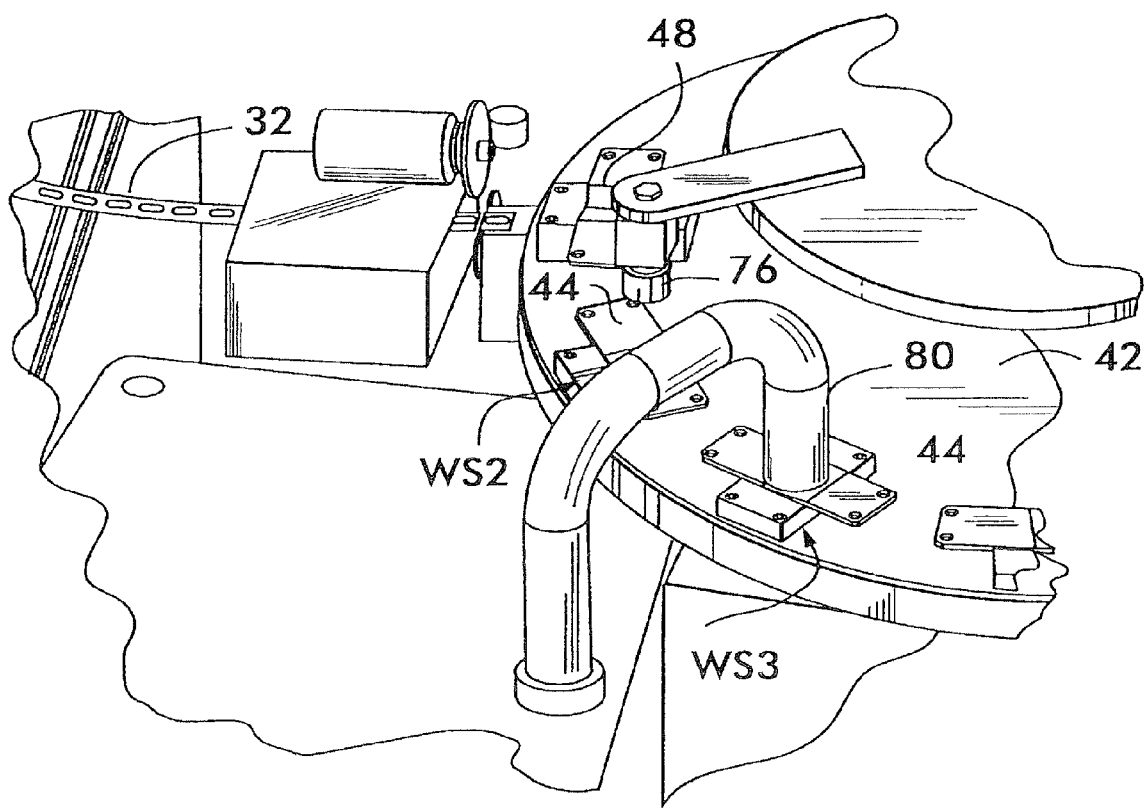
FIG. 5 is an illustration of work stations 2 and 3 of the encapsulation machine shown in FIG. 3.

With reference to FIG. 5, after placement of the pouch assembly 18 onto the tooling block 44 at work station one (WS1), the table 42 is preferably rotated to bring the pouch assembly 18 to work station two (WS2), where a vision camera 76 inspects the pouch 16 of the assembly 18, such as for a good seal and to determine if the ingredient section 12 has experienced breakage. Such visions systems are known in the art. The pouch assembly 18 can also be inspected by weight, as known in the art, to determine if the pouch assembly contains the desired amount of active ingredients. To accommodate situations in which the pouch assembly 18 is defective, the present embodiment can remove it at work station three WS3 where the table 42 brings the tablet/pouch assembly 18 under a vacuum transducer 80 which removes the pouch assembly by vacuum or other suitable means. If not defective, the tablet/pouch assembly 18 continues with the rotation of the table 42 to work station four (WS4).

Figure 6:
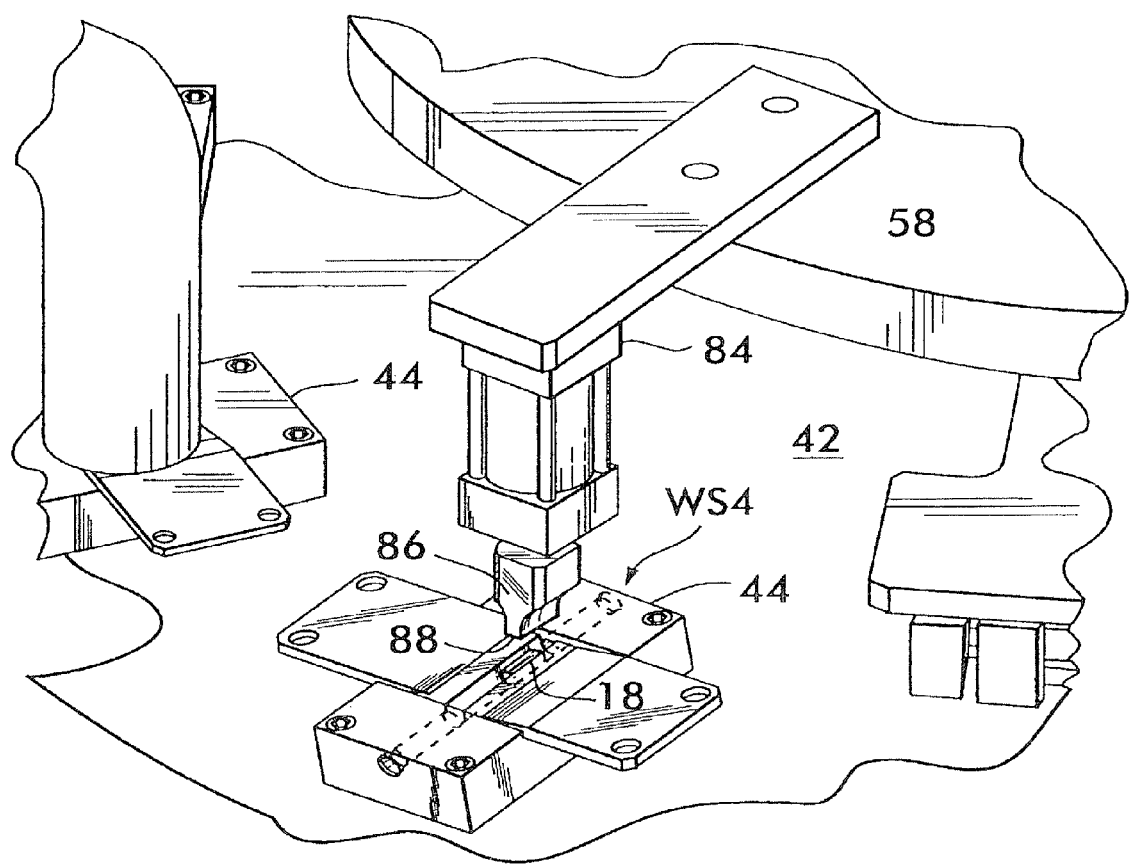
FIG. 6 is an illustration of work station 4 of the encapsulation machine.
Figure 6A:
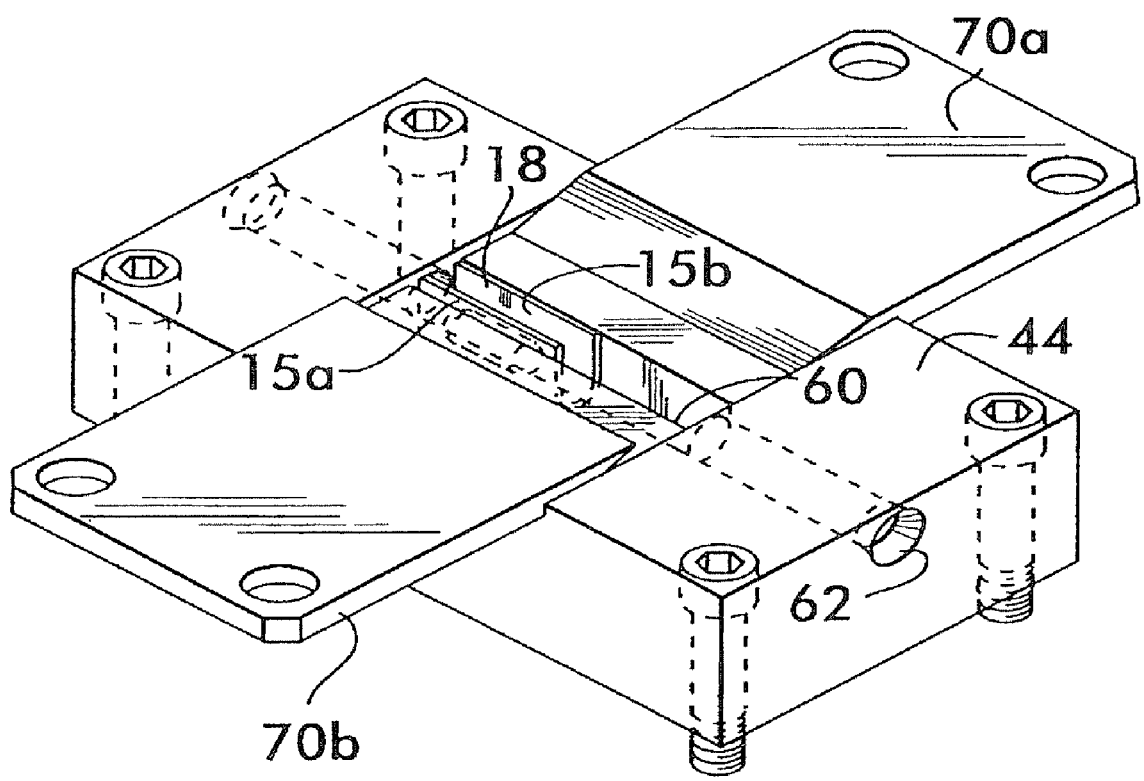
FIG. 6A shows the ingredient/pouch assembly within the tooling block at work station 4.

With reference to FIGS. 6 and 6A, at work station four (WS4) the pouch assembly 18 is inserted into the tooling block 44 to begin the folding of the pouch assembly 18. Supported above the pouch assembly 18 on the upper support 58 is an arm 84 having a push member, such as the illustrated ram 86. The ram 86 is extendable downward from the retracted position shown in FIG. 6 to an extended position whereby it pushes the pouch assembly 18 down through the tooling pocket 60 and into the cylindrical passageway 62. The ram 86 preferably has a head 88 shaped to correspond with the shape of the top of the pouch assembly 18, more preferably by corresponding to the top shape of the active ingredient section 12, to avoid damaging the pouch assembly 18. Different rams or similar structures 86 with different head shapes may be used for correspondingly different shapes of the assembly 18.

With reference to FIG. 6A, it is seen that as the pouch assembly 18 is pushed downward into the tooling pocket 60, at least a portion of the side flaps 15a, 15b of the pouch 16 are forced/folded upward about the ingredient section 12, leaving the side flaps 15a, 15b extending upwards. Preferably, at least a portion, and preferably a substantial portion of the side flaps extend out of the tooling pocket 60 in this position. Once the ram 86 is retracted, the table 42 moves the pouch assembly 18 (in the tool block) to work station five (WS5) for further folding.

Figure 7:
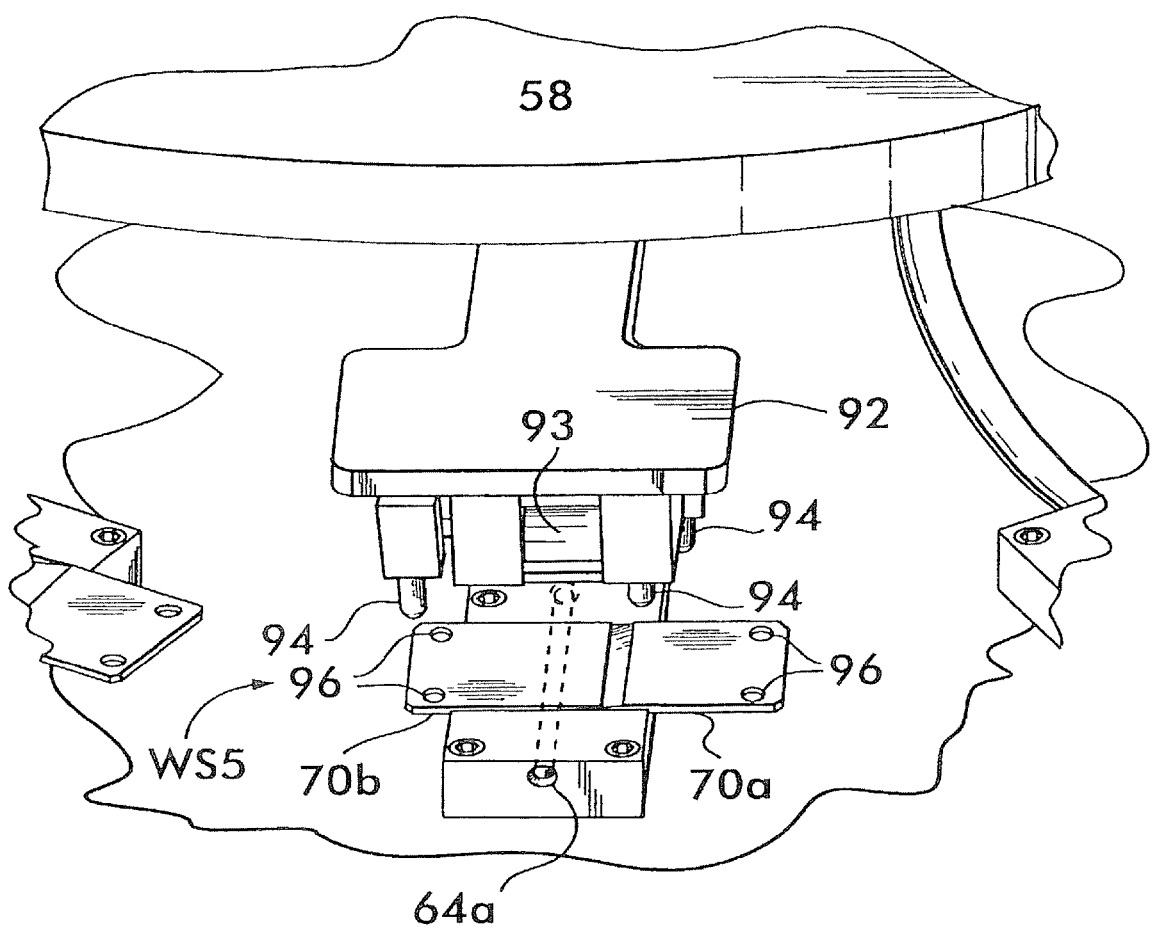
FIG. 7 is an illustration of work station 5 of the encapsulation machine.
Figure 7A:
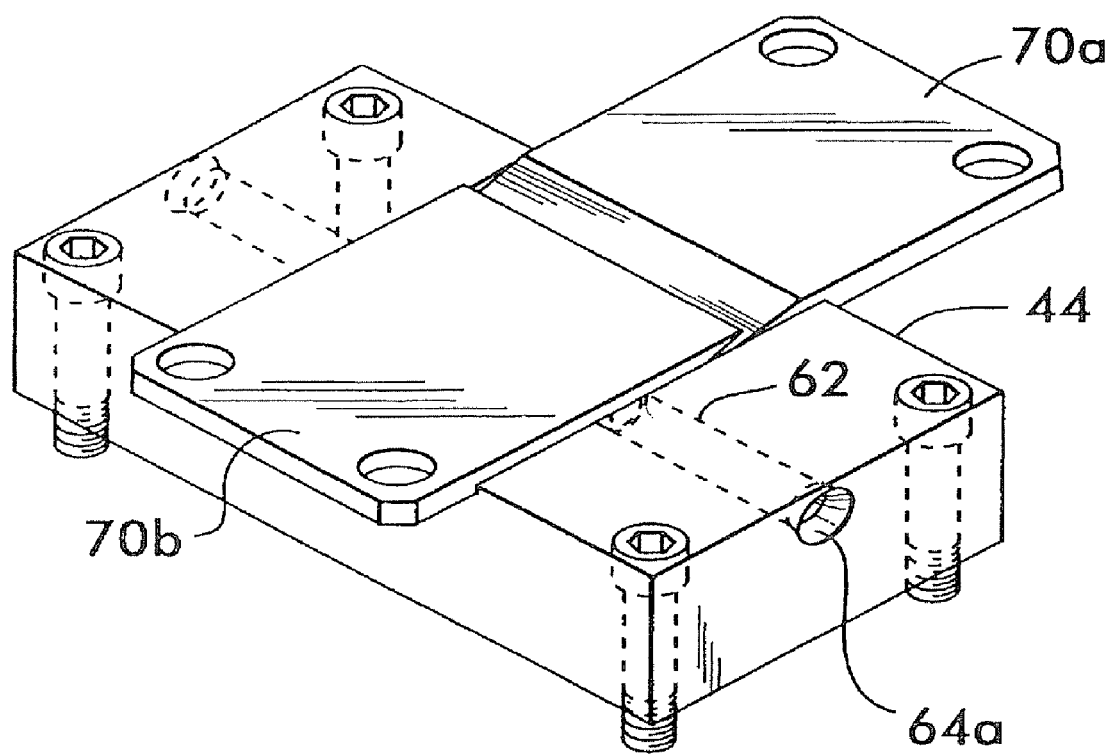
FIG. 7A shows the folding arms relative to the tooling block at work station 5 after the folding operation is completed.
Figure 7B:
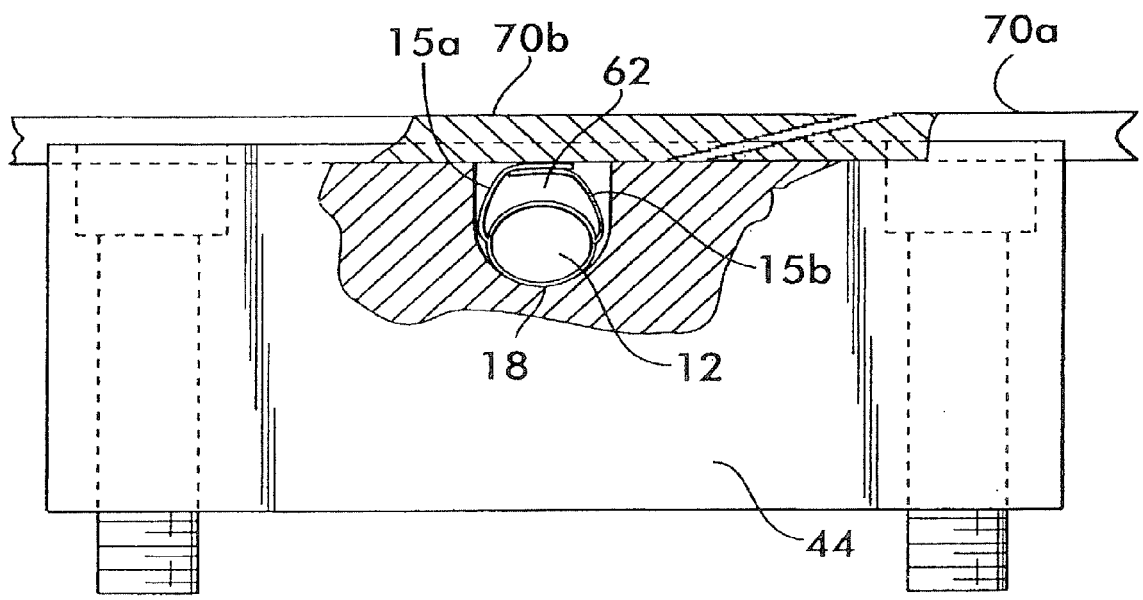
FIG. 7B is a side view showing the folded ingredient/pouch assembly shown in FIG. 7.

With reference to FIGS. 7, 7A and 7B, work station five (WS5) is where the final folding operation of the present embodiment takes place. An arm 92 at work station five has pins 94 for engaging the openings 96 in the folding arms 70a, 70b. For the final folding operation, the arm 92 is lowered so that the pins 94 can engage the openings in the folding arms. Any type of suitable actuator or motor device 93 may be used for moving the pins to move the arms. First, the right folding arm 70a is moved towards the left to fold the right side flap 15b of the pouch 16 approximately 90 degrees towards the left (see also FIG. 6A). Then the left folding arm 70b is moved to the right to fold the left side flap of the pouch 16 approximately 90 degrees to the right. The right folding arm 70a then retracts to clear the opposite end of the pouch assembly 18, and the left folding arm 70b moves to the right, preferably to fully cover and trap the folded pouch assembly 18 of within the passageway 62 as shown in FIG. 7B. The folded pouch assembly 18 is now ready for encapsulation.

Figure 8:
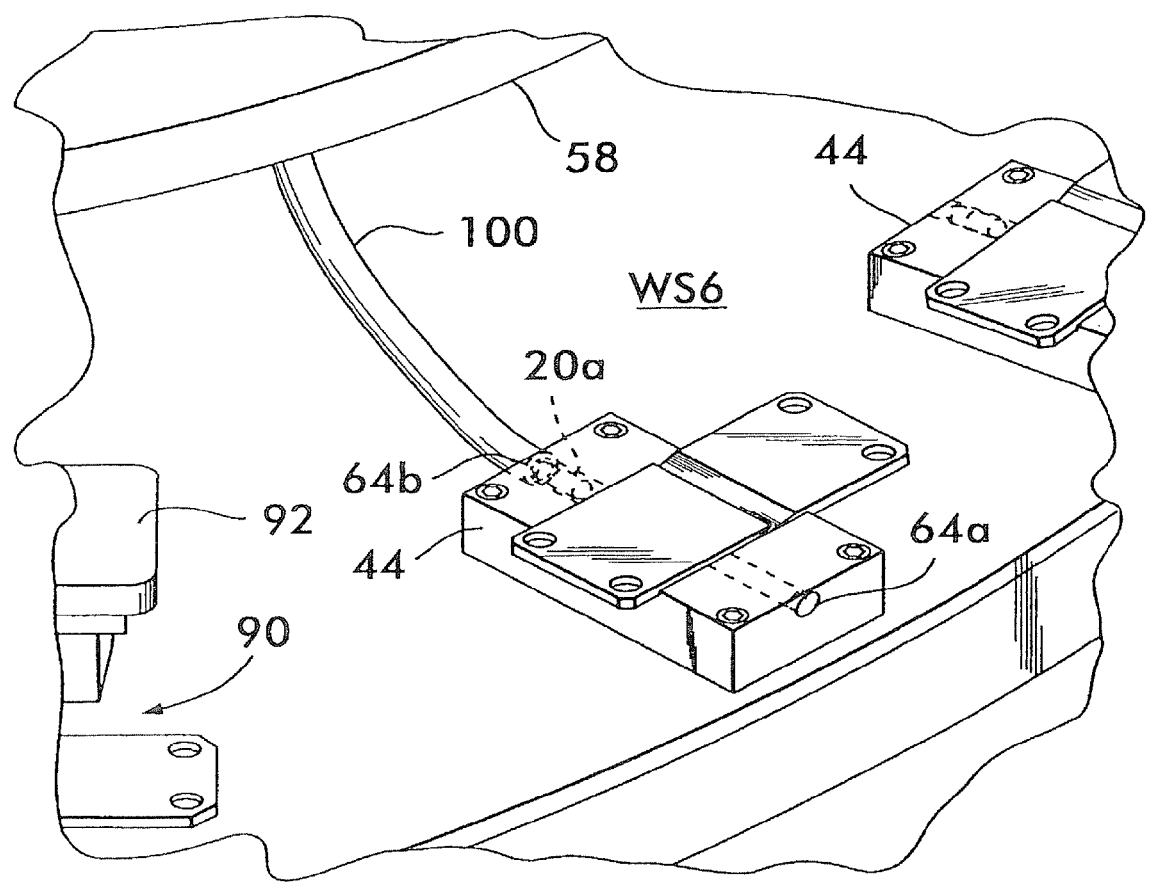
FIG. 8 is an illustration of work station 6 of the encapsulation machine where the gel capsule body is fed into the tooling block.
Figure 8A:
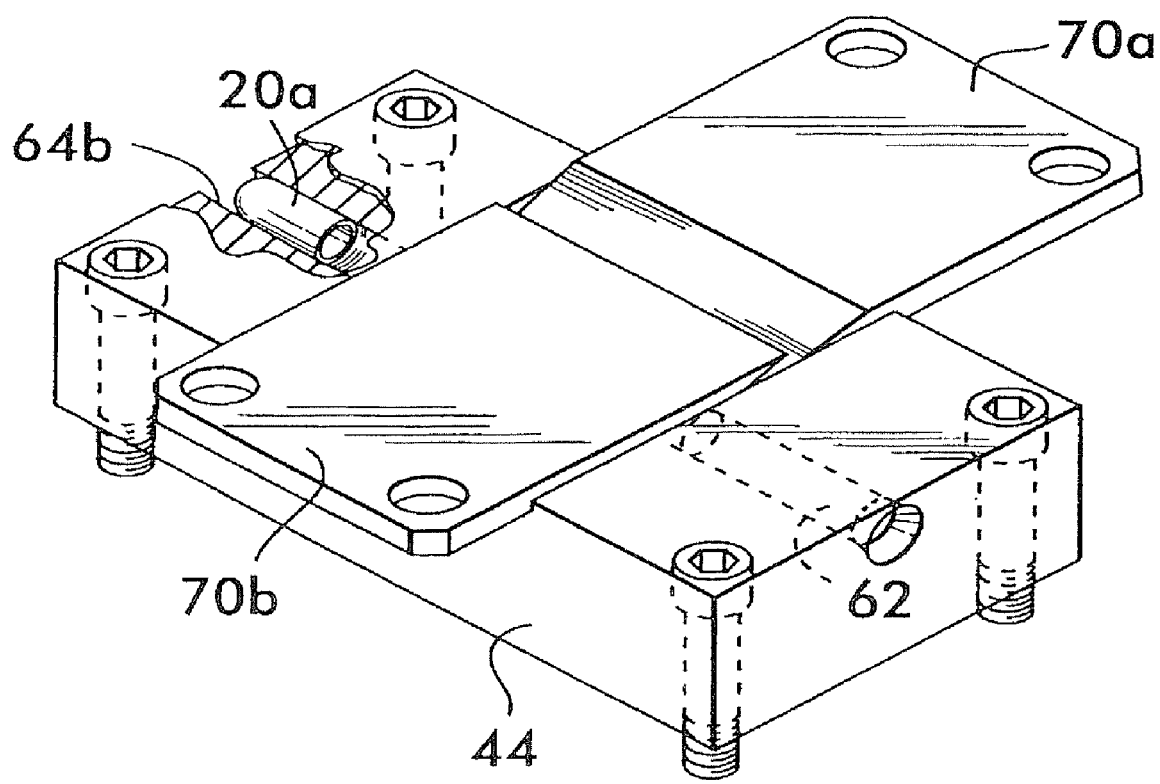
FIG. 8A is a detailed view of the tooling block at work station 6.

After further advancement of the table 42, at work station six (WS6), with reference to FIGS. 8 and 8A, the opening 64b to the passageway 62 on the back side of the tooling block 44 aligns with a feed tube 100 which delivers the gel capsule body 20a to the tooling block 44. A bowl feeder 102 (FIG. 3) supplies the gel capsule body 20a properly oriented through means as known in the art through the feed tube 100 to the tooling block 44 as shown.

Figure 9:
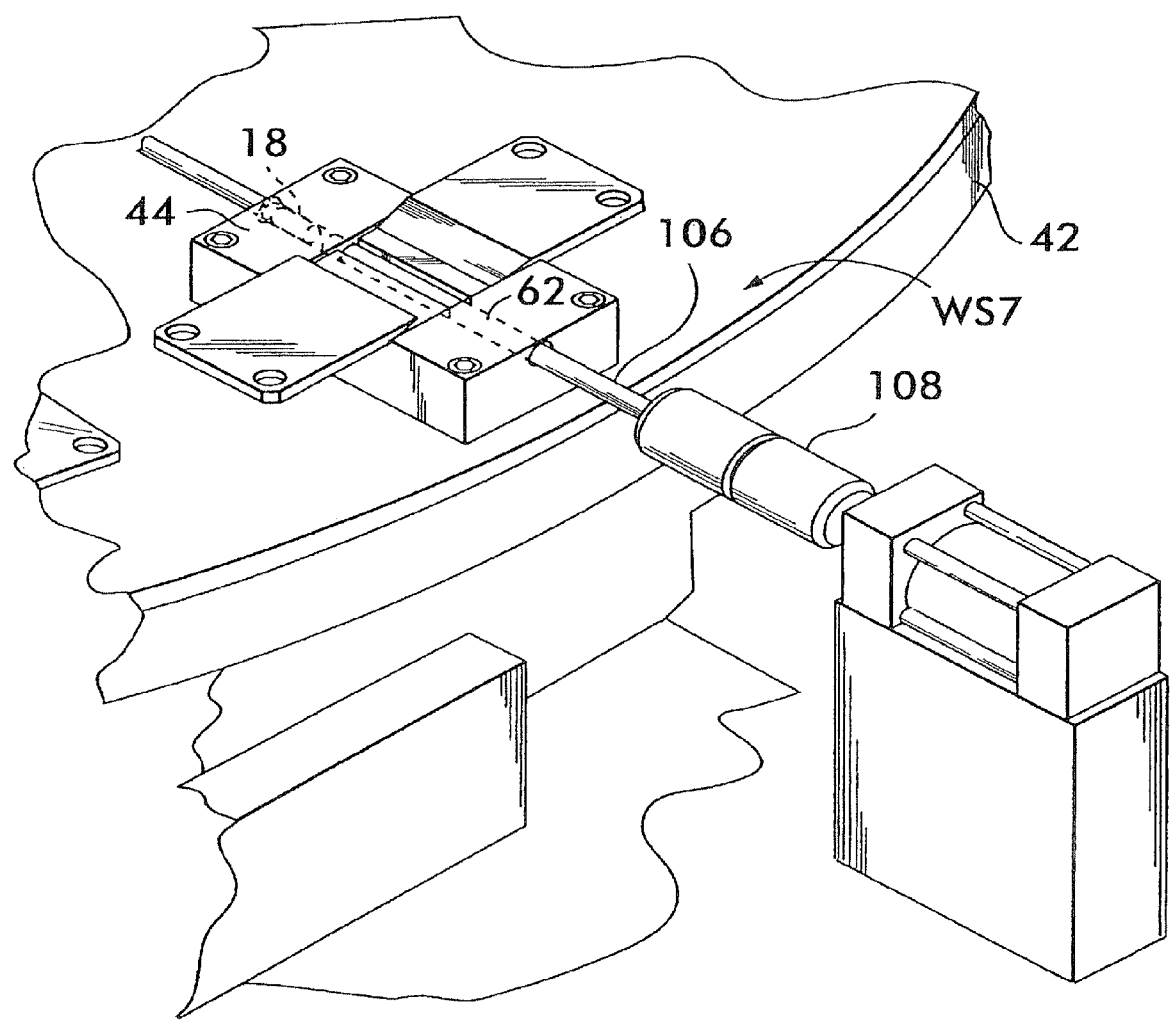
FIG. 9 is an illustration of work station 7 of the encapsulation machine where the folded ingredient/pouch assembly is inserted into the gel capsule body.
Figure 9A:
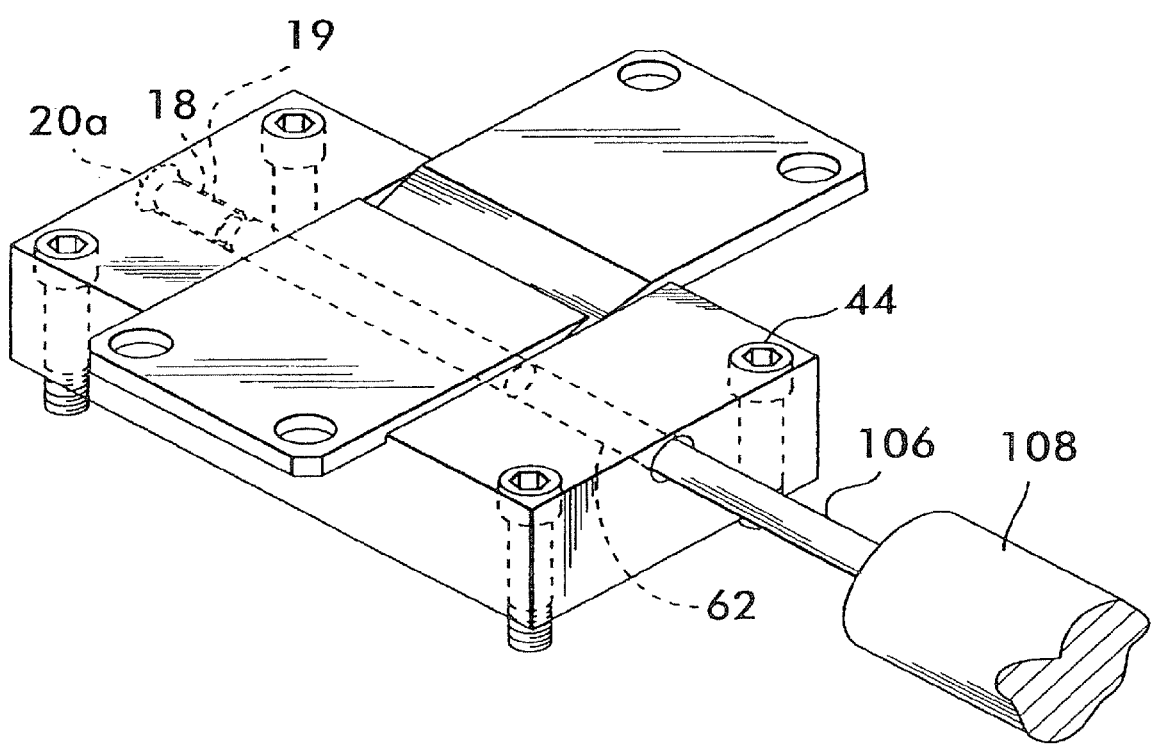
FIG. 9A is a detailed view of the tooling block at work station 7.

The tooling block 44 with the gel cap 20a next proceeds to work station seven (WS7) where the folded pouch assembly 18 is inserted into the gel cap body 20a. With reference to FIGS. 9 and 9A, a push member, such as a horizontal push rod or ram 106 extends from an actuator 108 through the passageway 62 to push the folded pouch assembly 18 into the gel capsule body 20a. A holding means, such as a blocking plate or an actuated back up push rod as shown in FIG. 9, similar to the push rod 106, can be moved to the back opening 64a to prevent the capsule body 20a from moving when the pouch assembly is pushed into the capsule body 20a. The ram 106, and any back-up push rod is then retracted to clear the tooling block 44. The ram actuator 108 is preferably supported on the frame 43 of machine 24.

Figure 10:
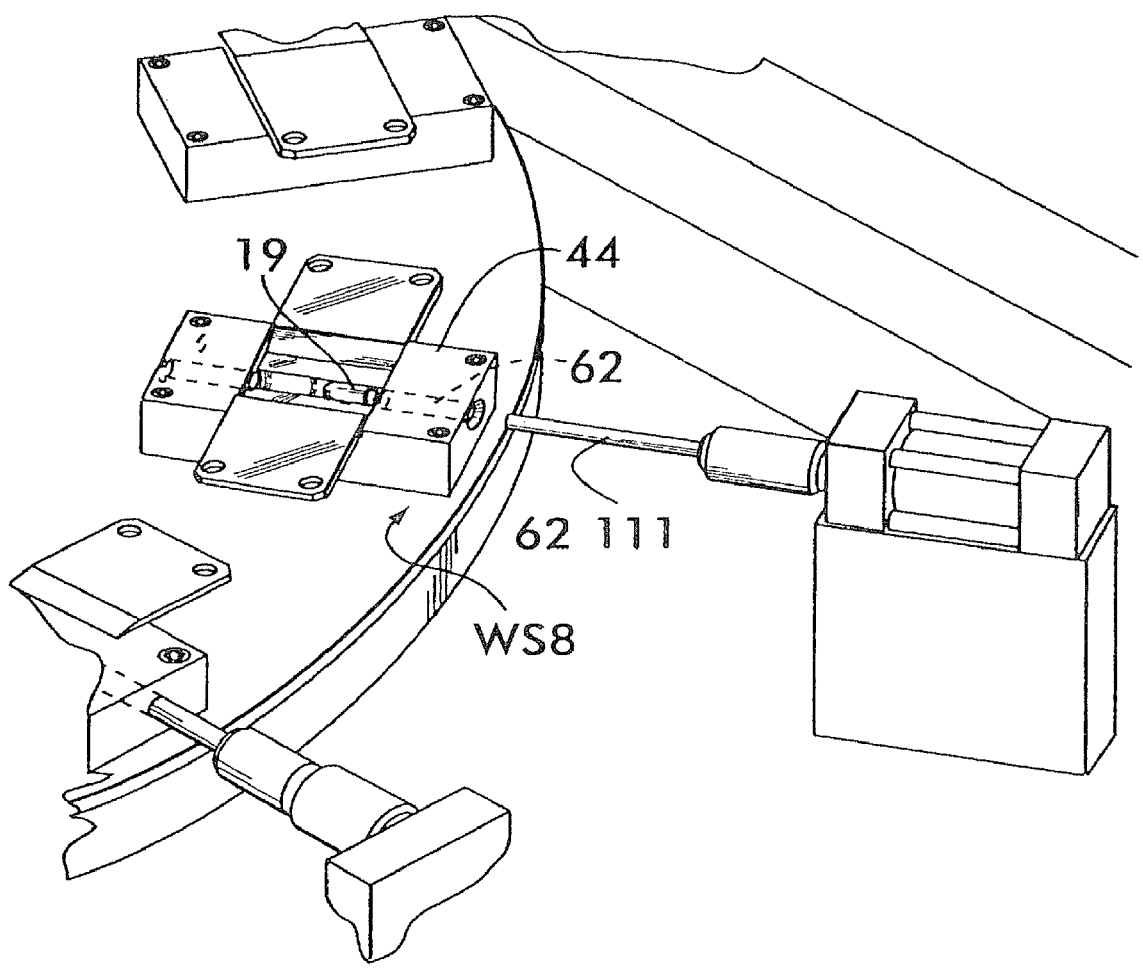
FIG. 10 is an illustration of work station 8 of the encapsulation machine where the folded ingredient/pouch assembly is repositioned for further assembly operations.

At work station eight (WS8), with reference to FIG. 10, the folded pouch assembly 18 in the capsule body 20a (pouch/capsule body 19) is repositioned within the passageway 62 for further processing. Here a horizontal ram 111 supported on the frame 43 extends through the passageway 62 to transfer the pouch/capsule body assembly 19 out the back side of the tooling block 44 and into a pick and place gripper (not shown). The pick and place gripper then transfers the pouch/capsule body assembly 19 to the front end of the tooling pocket 60 and into the passageway 62 as shown.

Figure 11:
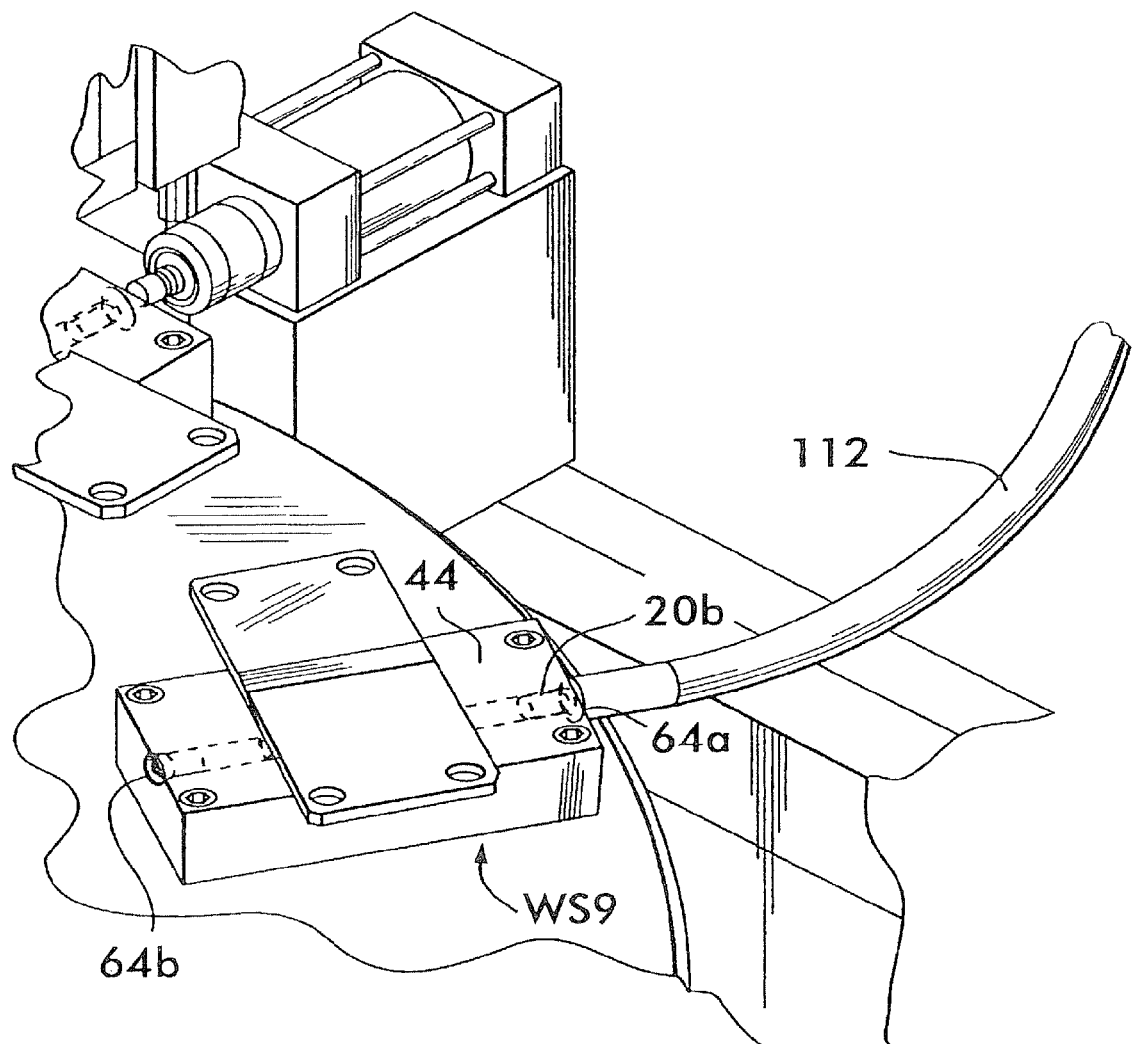
FIG. 11 is an illustration of work station 9 of the encapsulation machine where the gel capsule cap is fed into the tooling block.
Figure 11A:
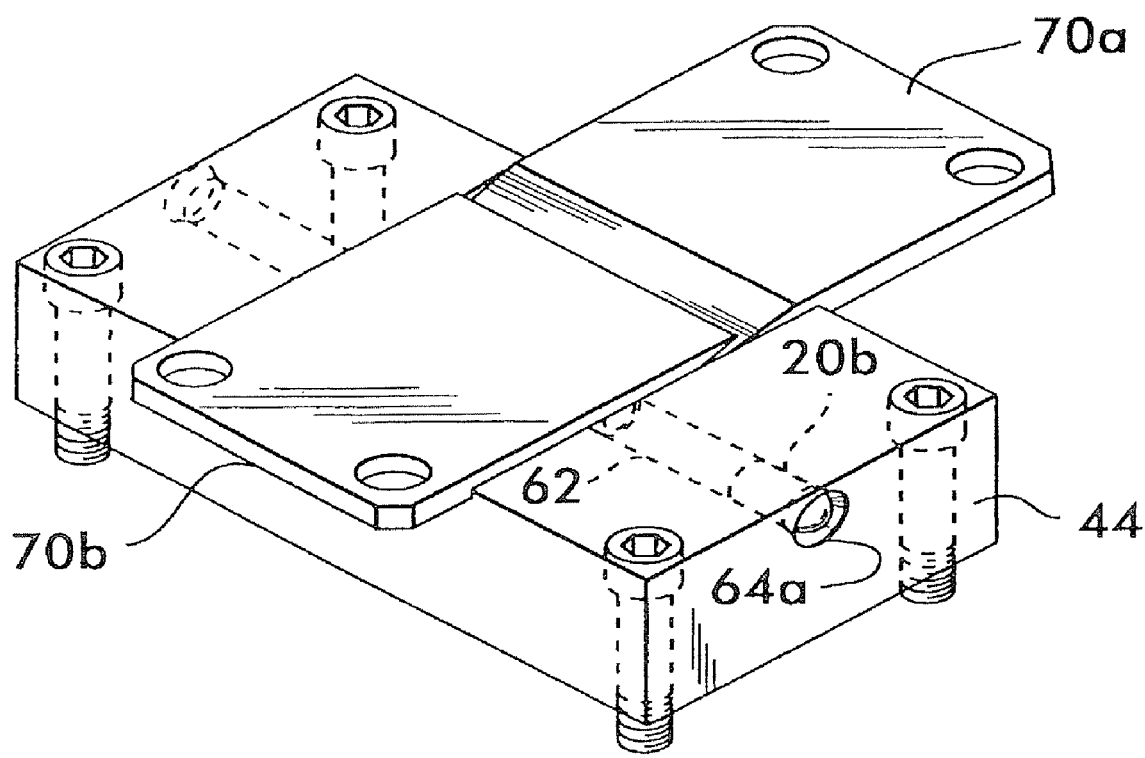
FIG. 11A is a detailed view of the tooling block at work station 9.

At work station nine (WS9), with reference to FIGS. 11 and 11a, the front opening 64a of the passageway 62 aligns with a second feed tube 112 through which the capsule cap 20b is delivered to the tooling block 44. A bowl feeder 114 supplies a single capsule cap 20b through the feed tube 112 as shown (see FIG. 3).

Figure 12:
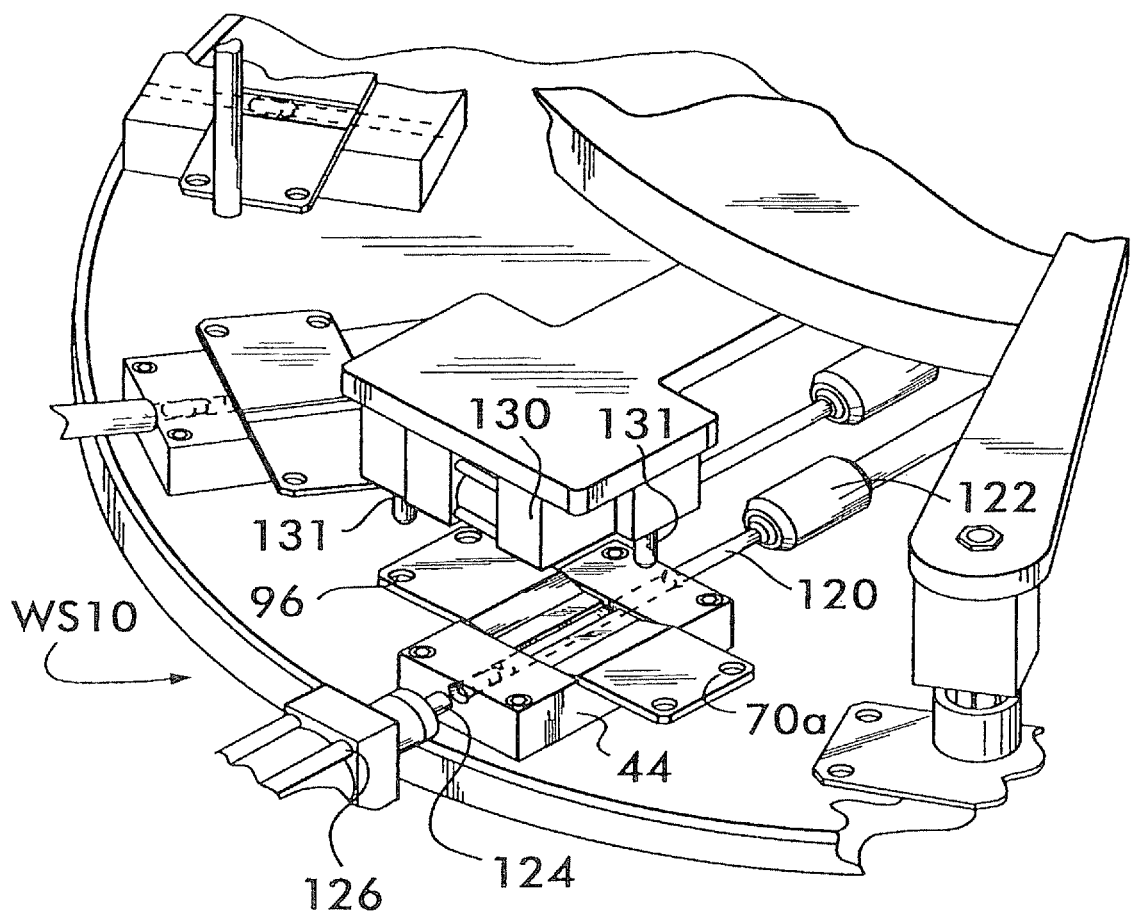
FIG. 12 is an illustration of work station 10 of the encapsulation machine where the folded ingredient/pouch assembly is inserted into the gel capsule cap.
Figure 12A:
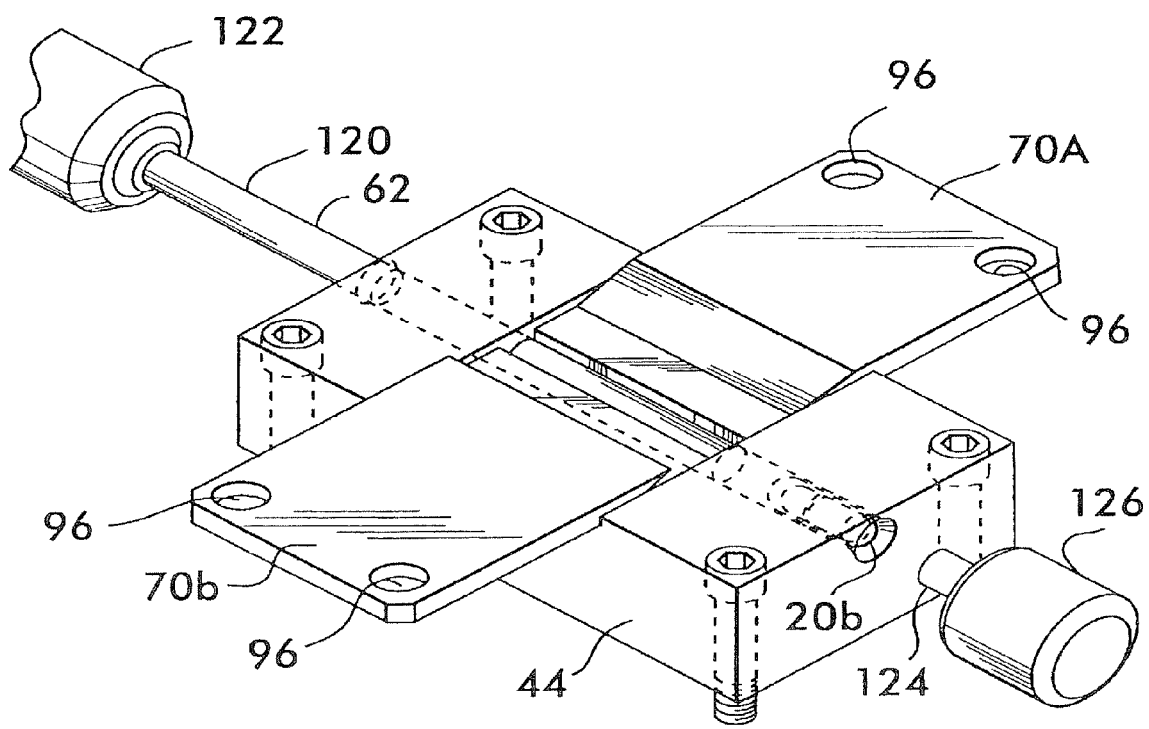
FIG. 12A is a detailed view of the tooling block at work station 10.

The tooling block 44 next proceeds to work station ten (WS10) where the pouch/capsule body assembly 19 is inserted into the capsule cap 20b. With reference to FIGS. 12 and 12A, a rear horizontal push rod or ram 120 extends from an actuator 122 through the passageway 62 to push the pouch/capsule body assembly 19 into the capsule cap 20b, which is held in place by a front horizontal push rod or ram 124 which extends from the front actuator 126. The front edges of the two rams are preferably shaped to correspond with the shape of the capsule sections to prevent damage. After the capsule body and cap 20a, 20b are attached to one another, preferably locked together as known in the art, both rams 120, 124 are retracted to clear the tooling block 44. Next the two folding arms 70a, 70b are retracted by an actuated arm 130 having pins 131 for interfacing with the openings 96 of the folding arms 70a, 70b.

Figure 10A:
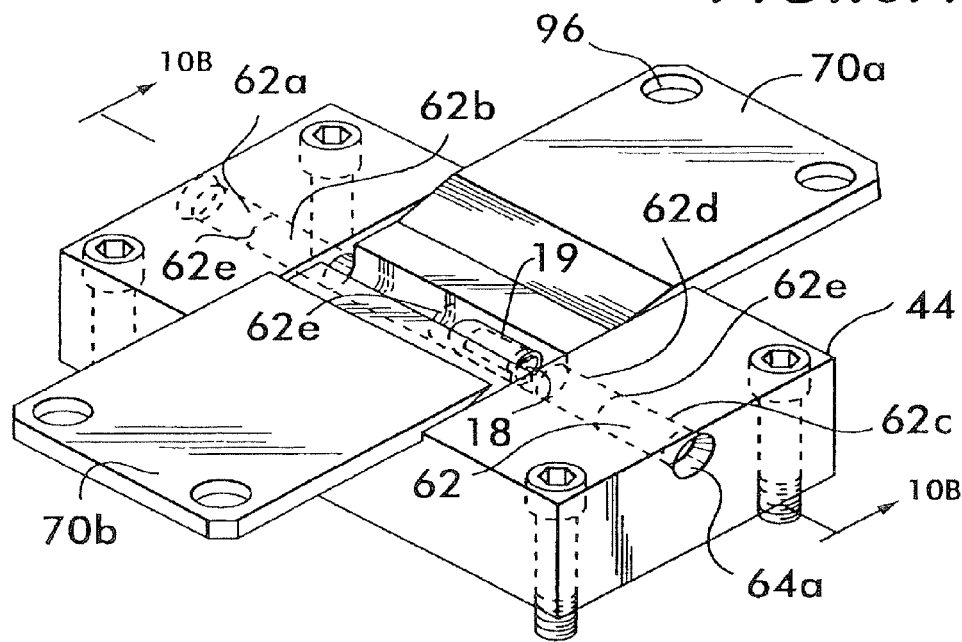
FIG. 10A is a detailed view of the tooling block at work station 8.
Figure 10B:
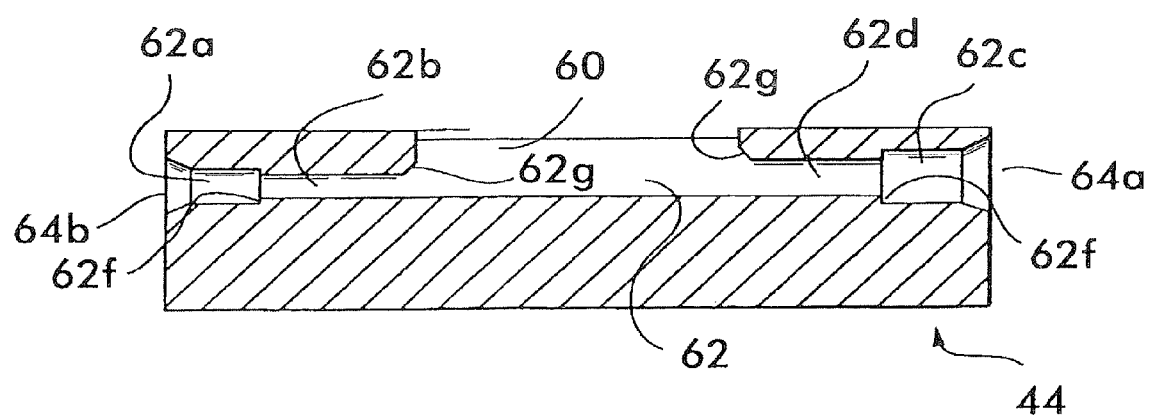
FIG. 10B is a cross sectional view taken along line 10B-10B of FIG. 10A.

With reference to FIGS. 10A and 10B, the cylindrical passageway 62 is preferably not of uniform diameter, but can have sections of different diameters depending on the process step to be carried out therein. For example, in the illustrated embodiment, section 62a of the passageway, at the end 64b, is sized to receive the capsule body 20a at WS6. The passageway section 62b, beginning in the portion of the passageway 62 under the upper portion the pocket 60 that holds the pouch assembly as shown in FIG. 6a and extending to the section 62a, is sized no larger than the inner diameter of the capsule body 20b, and preferably slightly smaller, to allow easy insertion of the wrapped pouch assembly 18 into the capsule body 20a. The passage section 62c at the end 64a, is sized to receive the capsule cap 20b at WS9. The passageway section 62d, beginning in the portion of the passageway 62 under the upper portion of the pocket 60 that receives that wrapped pouch/capsule body 19 at WS8 (FIG. 10) and extending to the section 62c, is sized for the diameter of the capsule body 20b, but smaller than the diameter of section 62c to allow easy insertion of the capsule body 20a into the capsule cap 20b. Preferable locations of changes 62e in diameter between the sections 62a, 62b, 62c and 62d are shown in dotted line in FIG. 10A. It is also understood that the change in diameter from the passageway section 62a to 62b acts as a shoulder 62f to stop movement of the capsule body 20b when delivered to the passageway 62 by tube 100. Likewise, the change in diameter from the passageway section 62c to 62d acts as a shoulder 62f to stop movement of the capsule cap 20a when delivered to the passageway 62 by tube 112. Tapered sections 62g can be provided to help smooth the transfer of the pouch assembly and capsule body 20a within the passageway 62. Other suitable configurations for the passageway 62 can be used.

Figure 13:
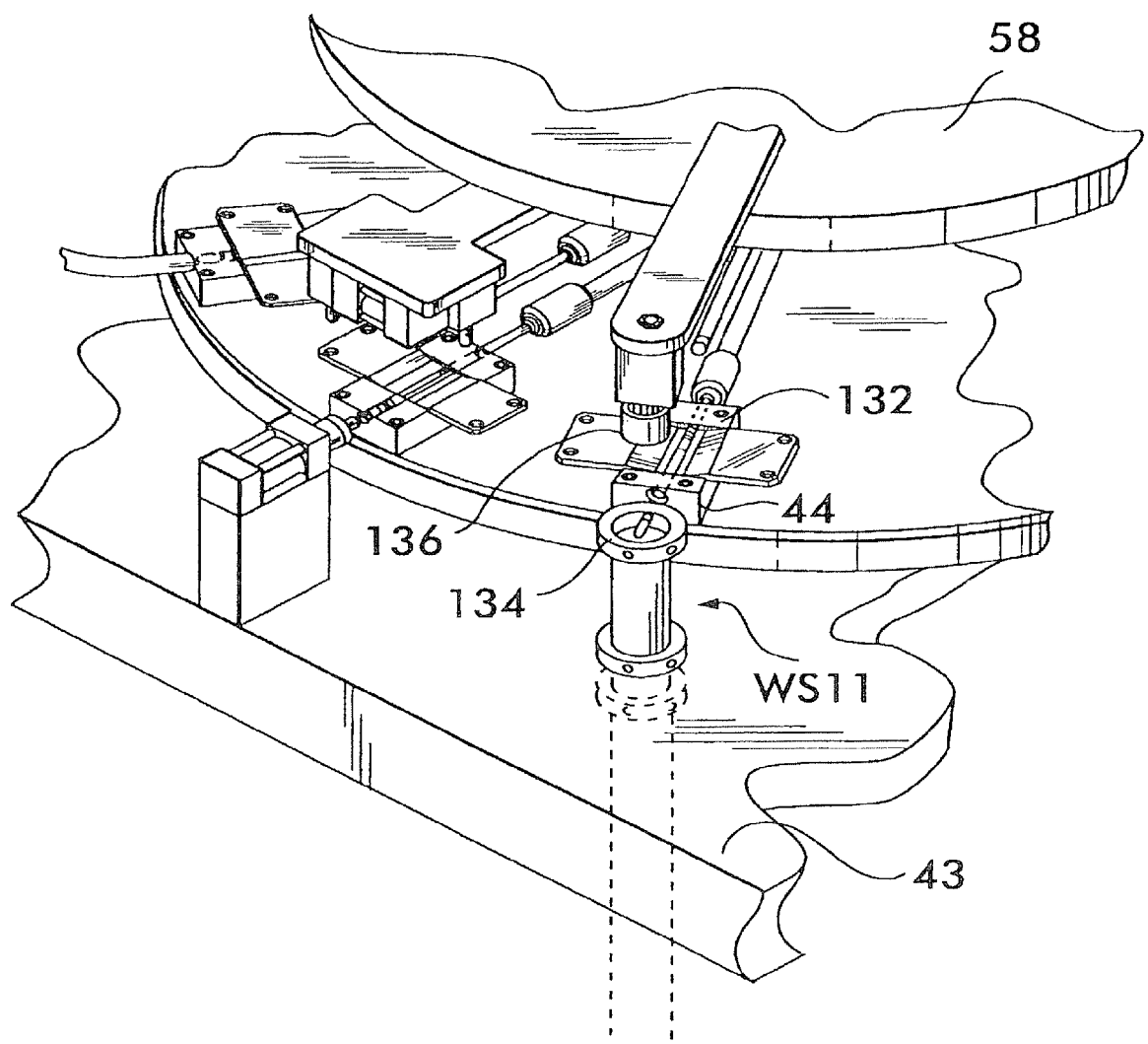
FIG. 13 is an illustration of work station 11 of the encapsulation machine where the completed retard form is inspected and directed to an appropriate container.
Figure 13A:
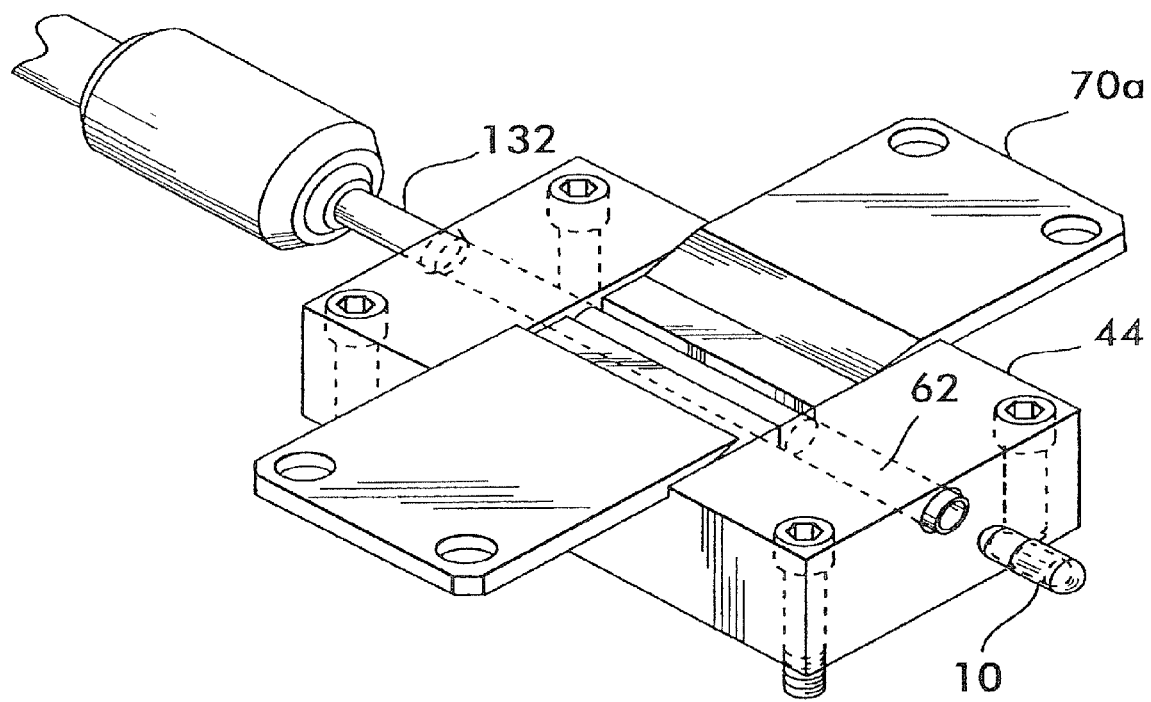
FIG. 13A is a detailed view of the tooling block at work station 11.

With reference to FIGS. 13 and 13A, a final process step, which takes place at work station eleven (WS11), is described. Here, the final gastro-retentive device 10 (the combined capsule/pouch assembly) is inspected and directed to the appropriate container. A horizontal push rod 132 is extended into the passageway 62 to expel the gastro-retentive device 10 from the tooling block 44 onto a support shelf 134 where it can be inspected by a camera 136. If the assembly 10 is acceptable, the push rod 132 extends further to push the gastro-retentive device 10 into the acceptable bin, otherwise, if rejected, the gastro-retentive device 10 is ejected into a reject container. This can be accomplished with a diverter arm (not shown) controlled by a controller which diverts the assembly between two chutes or troughs that directs the assembly to the acceptable bin or the reject container or by any other suitable means.

The table 42 then rotates to bring the tooling block 44 back to work station one (WS1) where a new pouch assembly 18 is received for encapsulation. It is seen that the table 42 has multiple tooling blocks 44 for processing multiple pouch assemblies 18 in a continuous automated process.

Figure 14:
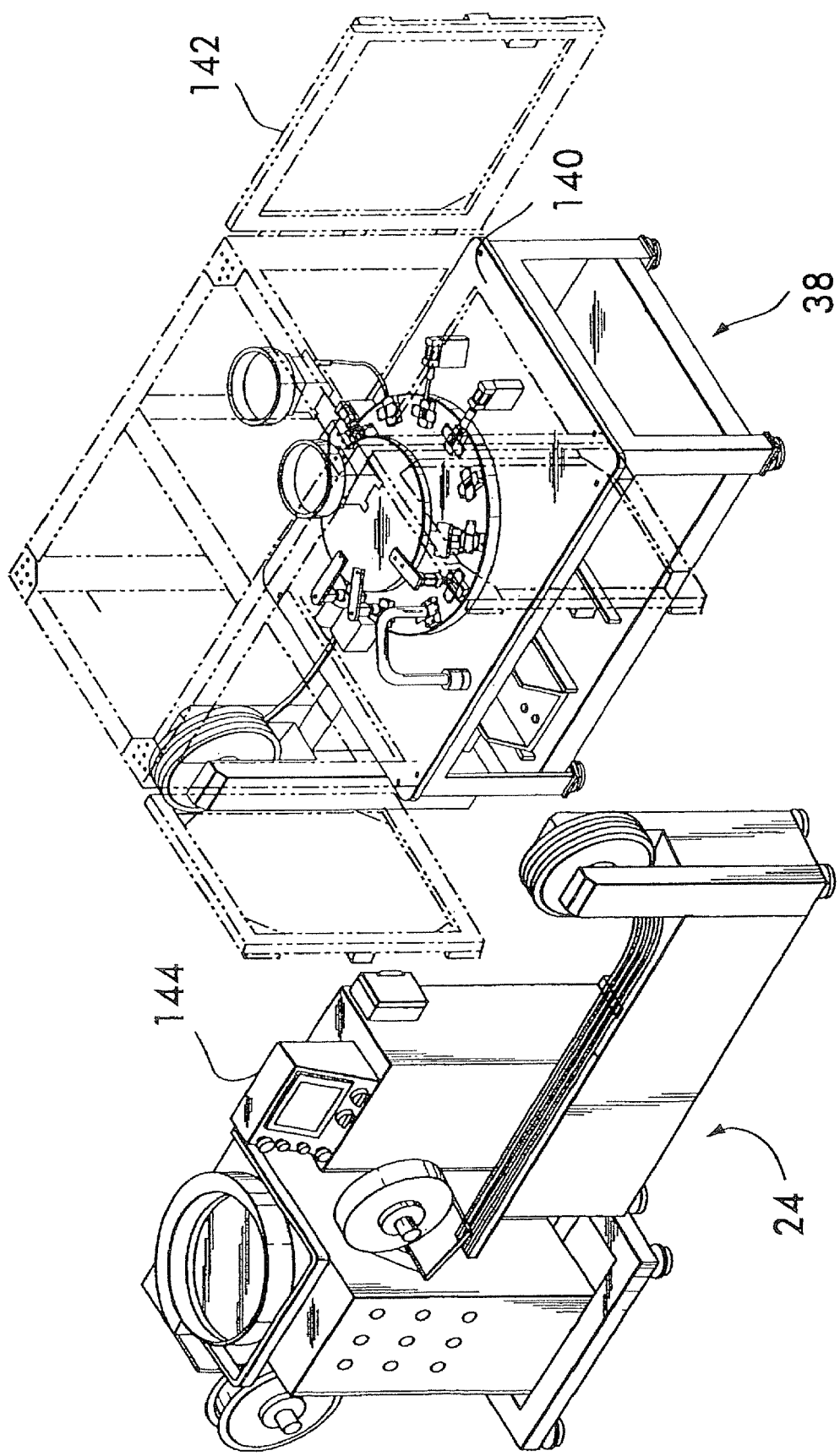
FIG. 14 shows the ingredient/pouch packaging machine and the encapsulation machine, the encapsulation machine being shown within an enclosure.

With reference to FIG. 14, the machines can be encased within a housing 140 having interlocked safety doors 142 and covers to prevent inadvertent injury to personnel or product contamination. Any suitable control system for controlling the various process steps may be used.

Any suitable materials as known in the art may be used for the various components. For example, ANSI 316 Stainless Steel may be used for product contact surfaces. These surfaces and associated welds are preferably polished to a number 7 mirror finish. ANSI 304 Stainless Steel may be used elsewhere. A number 4 finish can be provided for naked (non-shed) metallic non-product contact surfaces and welds.

The present invention as described above provides an economical means of producing an advantageous gastro-retentive device 10.

While particular embodiments of the invention are described herein, it is not intended to limit the invention to such disclosure and changes and modifications may be incorporated and embodied within the scope of the invention.

What is claimed is:

1. A process for making a gastro-retentive device having at least the following components:
  1) an ingredient section,
  2) a membrane combined with and surrounding the ingredient section so as to form a pouch assembly having at least one flap extending from the ingredient section, and a capsule surrounding the pouch assembly and which is capable of disintegrating upon contact with bodily fluids to release the pouch assembly, said capsule having first and second capsule sections; said process comprising the following automated steps:
  (A) providing a pouch assembly;
  (B) placing said pouch assembly on a tooling block having a surface and a pocket formed therein which is sized for receiving said pouch assembly, said ingredient section of said pouch assembly being placed over said pocket with said flap extending away from said pocket;
  (C) folding said flap by pushing said ingredient section of said pouch assembly into said pocket so as to fold said flap around said ingredient section;
  (D) inserting said pouch assembly folded in step (C) into the first capsule section to form a pouch/first cap assembly; and
  (E) connecting said pouch/first capsule assembly to the second capsule section to fully encapsulate said pouch assembly.

2. The process for making a gastro-retentive device of claim 1 further comprising the steps of: (A)(i) providing a strip of said pouch assemblies; and (A)(ii) separating a single pouch assembly from said strip.

3. The process for making a gastro-retentive device in accordance with claim 1 wherein step (C) further comprises the step of: (C)(i) moving a member over the surface of said tooling block to fold said flap extending out of said pocket.

4. The process for making a gastro-retentive device of claim 3 wherein step (C) further comprises the step of: (C)(ii) moving a second member over the surface of said tooling block to fold a second flap extending out of said pocket.

5. The process for making a gastro-retentive device in accordance with claim 1 wherein step (E) comprises the step of moving said folded pouch assembly through a passageway into said first capsule section, said passageway extending through said tool block and is connected to and positioned below said pocket, said pouch assembly being moved into said passageway through said pocket during step (C).

6. The process for making a gastro-retentive device in accordance with claim 5 wherein step (F) comprises the step of moving said first capsule section/folded pouch formed in step (E) through said passageway of said tool block into said second capsule section.

7. The process for making a gastro-retentive device in accordance with claim 1 wherein at least two of said (A) through (E) take place at different work stations.

8. The process for making a gastro-retentive device in accordance with claim 7, wherein multiple said tooling blocks are provided, and wherein each of said tooling blocks are moved to each of said locations for carrying out the process steps.

* * * * *